United States Patent
Oberlaender et al.

(10) Patent No.: US 8,702,740 B2
(45) Date of Patent: Apr. 22, 2014

(54) MEDICAL PUNCH

(75) Inventors: Martin Oberlaender, Engen (DE); Michael Sauer, Tuttlingen (DE); Uwe Bacher, Tuttlingen (DE); Michael Staehler, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 452 days.

(21) Appl. No.: 12/793,964

(22) Filed: Jun. 4, 2010

(65) Prior Publication Data

US 2010/0312265 A1  Dec. 9, 2010

(30) Foreign Application Priority Data

Jun. 6, 2009 (DE) .......... 10 2009 024 124

(51) Int. Cl.
*A61B 17/32* (2006.01)

(52) U.S. Cl.
USPC ............................................. 606/184

(58) Field of Classification Search
USPC .............. 30/113.1–113.3; 600/564, 566, 567; 606/83, 131, 133, 167, 170, 174, 184, 606/185, 187
See application file for complete search history.

(56) References Cited

U.S. PATENT DOCUMENTS

| 4,722,338 | A | * | 2/1988 | Wright et al. ............. 606/83 |
| 4,777,948 | A | * | 10/1988 | Wright ............. 606/83 |
| 5,484,441 | A | | 1/1996 | Koros et al. |
| 2006/0149271 | A1 | * | 7/2006 | Michelson ............. 606/83 |

FOREIGN PATENT DOCUMENTS

| DE | 2808911 B1 | 3/1979 |
| DE | 8518482 U1 | 9/1985 |
| DE | 4445674 A1 | 8/1995 |
| DE | 10049060 A1 | 4/2002 |
| DE | 69533960 T2 | 1/2006 |
| DE | 60023538 T2 | 7/2006 |
| WO | 2007120063 A2 | 10/2007 |

OTHER PUBLICATIONS

German Search Report; Application No. 10 2009 024 124.8; Mar. 17, 2010; 4 pages.
European Search Report; Application No. EP 10 00 5676; Sep. 23, 2010; 7 pages.

* cited by examiner

*Primary Examiner* — Ashley Fishback
(74) *Attorney, Agent, or Firm* — St. Onge Steward Johnston & Reens LLC

(57) ABSTRACT

A medical punch with a hollow shaft, a tool point that is positioned on the distal end of the shaft and includes a rigid cutting part and a cutting part that can slide with respect to the rigid cutting part, and with a handle positioned on the proximal end of the shaft, such that the displaceable cutting part and the handle are operatively connected with one another by a push/pull device that is displaceably mounted in the hollow shaft and an anti-tilt mechanism is positioned on the tool point to stabilize the cutting parts in their axially parallel alignment to one another. The rigid cutting part includes a sleeve-shaped proximal portion that encloses the displaceable cutting part and a distal punch portion configured as a single unit with the sleeve-shaped portion and that the rigid cutting part should be detachably connected with the hollow shaft by a coupling mechanism formed on the sleeve-shaped portion.

6 Claims, 3 Drawing Sheets

Stand der Technik

MEDICAL PUNCH

CROSS-REFERENCE TO RELATED APPLICATIONS

The present application claims priority of German patent application No. 10 2009 024 124.8 filed on Jun. 6, 2009.

FIELD OF THE INVENTION

The invention relates to a medical punch with a hollow shaft, a tool point that is positioned on the distal end of the shaft and consists of a rigid cutting part and a cutting part that can slide with respect to the rigid cutting part, and a handle positioned on the proximal end of the shaft, such that the displaceable cutting part and the handle are operatively connected with one another by a push/pull device that is displaceably mounted in the hollow shaft and an anti-tilt mechanism, which stabilizes the cutting parts in their axially parallel alignment with one another, is positioned on the tool point.

BACKGROUND OF THE INVENTION

Medical punches are cutting tools with a rigid cutting edge and a cutting edge that can slide with respect to the rigid cutting edge, such that the two cutting edges are not capable of pivoting with respect to one another around a pivot point, as with a scissors or the like, but rather as a rule can be displaced horizontally with respect to one another.

With medical punches common in the art, the instrument shaft is configured as a hollow shaft in which a push/pull device, which is connected with the displaceable cutting edge and can be driven by the handle, is displaceably mounted. These punches have thoroughly proven themselves in the art, but in practice, in particular with stamps whose cutting edges are configured at an incline of 45 degrees with respect to the instrument's longitudinal axis, the cutting edges can go out of alignment when the cutting edges are slid into the punching or closing position. This slipping outward of the cutting edges from their axially parallel alignment to one another prevents a precise actuation of the medical punch.

To align the cutting edges of a medical punch axially parallel to one another, it is known, for instance from patent DE 28 08 911 C2, to secure the displaceable hollow outer tube with the rigid inner rod by means of a groove-and-tongue joint with respect to one another. The disadvantage of this known construction is, on the one hand, the high manufacturing cost of configuring the compatible anti-tilt mechanism and, on the other hand, the inflexibility concerning replacements of the cutting parts.

Consequently it is the object of the invention to design a medical punch of the aforementioned type in such a way that it is of simple construction and ensures a constantly exact guidance of the cutting parts with respect to one another.

SUMMARY OF THE INVENTION

This object is achieved according to the invention in a manner characterized in that rigid cutting part consists of a sleeve-shaped proximal portion that encloses the displaceable cutting part and a distal punch portion configured as a single unit with the sleeve-shaped part and that the rigid cutting part is detachably connected with the hollow shaft by a coupling mechanism configured on the sleeve-shaped part.

The inventive coupling of the rigid cutting part with the hollow shaft by a coupling mechanism configured on the sleeve-shaped part, for instance in the form of a bayonet connection, ensures that the inventive medical punch can be cleaned easily and thoroughly and in addition that the cutting parts can be replaced.

For inserting and guiding the displaceable cutting part, a guide track is advantageously configured in the sleeve-shaped part of the rigid cutting part; said guide track encloses, in essentially form-locking manner, the outer contour of the displaceable cutting part that is to be inserted. The properly aligned guidance of the displaceable cutting part in this guide track can be stabilized, according to the invention, by having at least one guide element that is configured on the displaceable cutting part and engages in a corresponding recess of the guide track of the rigid cutting part.

According to a first embodiment of the invention, it is proposed that the anti-tilt mechanism should be configured as a thrust bearing configured in the proximal area of one cutting part, for instance in the form of a bulge-type protrusion, with which the other cutting part is contiguous, thus ensuring a reciprocal stable positioning of the cutting parts with respect to one another.

According to a second embodiment of the invention, it is proposed that the anti-tilt mechanism should be configured as a guide pin that is positioned in the distal area on one cutting part and engages in a corresponding recess in the other cutting part. In this embodiment, the mutual stabilization is ensured by an essentially form-locking interlocking of partial areas of the two cutting parts.

It is proposed, with a third embodiment of the invention, that the anti-tilt mechanism should be composed of a sleeve surrounding both cutting parts in the proximal area. This type of configuration of the anti-tilt mechanism constitutes a particularly simple structural approach because the stable positioning of the cutting parts is achieved without particular structural adaptation of the cutting parts by the external pressure sleeve.

In order further to ensure that the axial displacement of the push/pull device exerted by the handle on the push/pull device is transmitted essentially free of play on the displaceable cutting part, it is proposed according to the invention that the displaceable cutting part should be connected with the push/pull device at least in force-fitted manner, so that the push/pull device can be inserted into the instrument shaft and can be withdrawn from the shaft through the distal end of the shaft.

According to a preferred embodiment of the invention, it is further proposed that the rigid cutting part and the displaceable cutting part should be connectable to form a single component by means of a sleeve-shaped enclosure that can be slid onto the sleeve-shaped part of the rigid cutting part. By means of this sleeve-shaped enclosure, the rigid cutting part is affixed undetachably to the displaceable cutting part that is mounted in the guide track of the rigid cutting part, so that one installation unit is created that can be affixed on the hollow instrument shaft by the coupling mechanism positioned on the sleeve-shaped proximal part of the rigid cutting part.

The enclosure that combines the displaceable cutting part and the rigid cutting part into a single component, according to a practical embodiment of the invention, at the same time constitutes the anti-tilt mechanism that stabilizes the two cutting parts with respect to one another and is configured as a sleeve.

It is finally proposed with the invention that a stop should be configured on the rigid cutting part to limit the displaceability of the displaceable cutting part in the distal direction.

Further properties and advantages of the invention can be seen from the appended illustrations in which several embodiments of an inventive medical punch are described as examples, without restricting the invention to these embodiments.

DETAILED DESCRIPTION OF THE INVENTION

Figure 1:
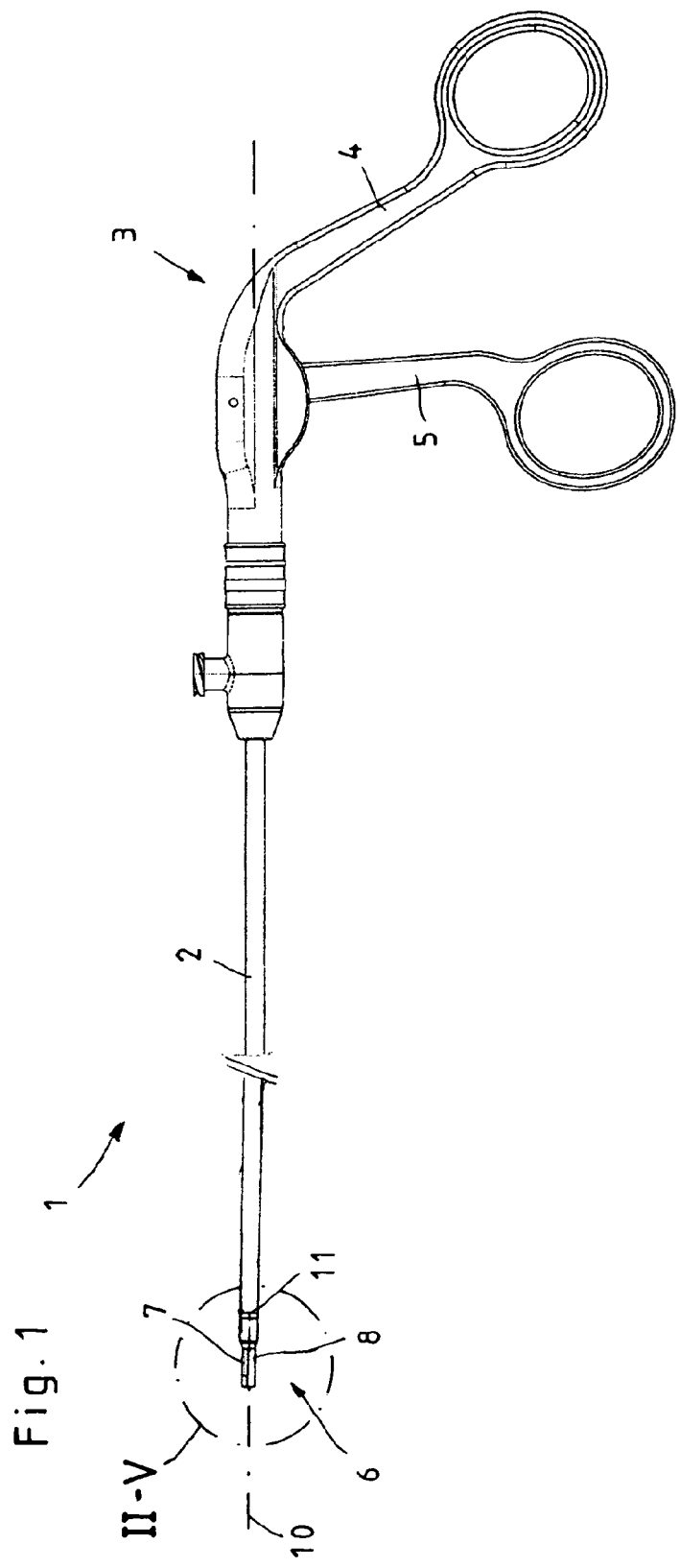
FIG. 1 is a schematic side view of an inventive medical punch.

The medical punch 1 shown complete in FIG. 1 consists essentially of a shaft 2 configured as a hollow shaft, on whose proximal end a handle 3 is positioned that consists of a rigid gripping part 4 and a gripping part 5 that can pivot with respect to the rigid gripping part 4. Positioned on the distal end of the shaft 2 is a tool point 6, which consists of a rigid cutting part 7 and a cutting part 8 that can slide with respect to the rigid cutting part 7, such that the displaceable cutting part 8 is operatively connected with the pivoting gripping part 5 of the handle 3 by means of a push/pull device 9 that is displaceably mounted in the shaft 2.

The displaceable cutting part 8 of the tool point 6 and the pivoting gripping part 5 of the handle 3 are operatively connected with one another by means of the push/pull device 9 in such a way that, thanks to the displacement of the pivoting gripping part 5 of the handle 3, the displaceable cutting part 8 can be moved into a closed punching position or conversely away from the rigid cutting part 7 into an open position by means of a displacement of the push/pull device 9 in the direction of the longitudinal axis 10 of the shaft 2 toward the rigid cutting part 7 of the tool point 6.

In the illustrated embodiment, pressing together the gripping parts 4 and 5 of the handle 3 causes a displacement of the push/pull device 9 in the proximal direction and thus a sliding of the displaceable cutting part 8 into the closed punching position of the tool point 6 shown in FIGS. 2 through 5. Conversely, pressing apart the gripping parts 4 and 5 of the handle 3 causes a displacement of the push/pull device 9 in the distal direction and thus a sliding of the displaceable cutting part 8 into the open position of the tool point 6 shown in FIG. 6, in which the displaceable cutting part 8 and the rigid cutting part 7 are at the greatest distance from one another.

The structure of the tool point 6 with the rigid cutting part 7 and the displaceable cutting part 8 can be seen in particular from the detailed views in FIGS. 2 through 6, which show four embodiments for configuring the tool point 6. In all cases the displaceable cutting part 8 forms the distal end of the push/pull device 9 that is displaceably mounted in the hollow shaft 2, such that the proximal end of the displaceable cutting part 8 and the distal end of the push/pull device 9 are connected in force-fitted manner with one another to ensure a transmission of the axial motion of the push/pull device 9 onto the displaceable cutting part 8 free of play.

As can further be seen from FIGS. 2 through 6, the rigid cutting part 7 can be detachably affixed on the shaft 2 by means of a coupling mechanism 11 configured as a bayonet connection.

Figure 2:
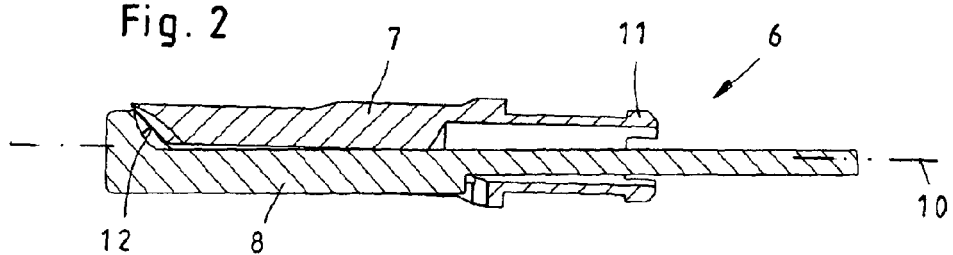
FIG. 2 is an enlarged cut-out view of detail I, showing a tool point according to the state of the art.

FIG. 2 shows a tool point 6 according to the state of the art, with a rigid cutting part 7 and a displaceable cutting part 8, both of whose cutting surfaces 12 are configured at a 45 degree angle to the longitudinal axis 10 of the shaft 2. Upon moving the displaceable cutting part 8 into the illustrated closed position, it frequently occurs that the cutting parts 7 and 8 move out of their axially parallel alignment to one another, as shown in FIG. 2. With the cutting parts 7 and 8 tilted with respect to one another in this way, it is not possible for the operator to make a calibrated actuation of the punch tool.

Figure 3:
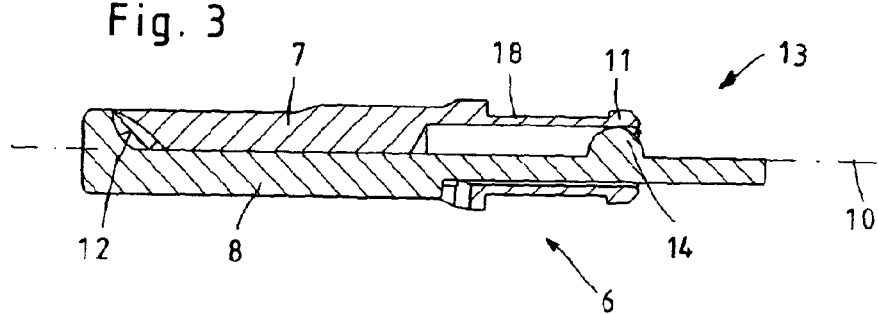
FIG. 3 is an enlarged cut-out view of detail III, showing a first inventive embodiment of a tool point.
Figure 4:
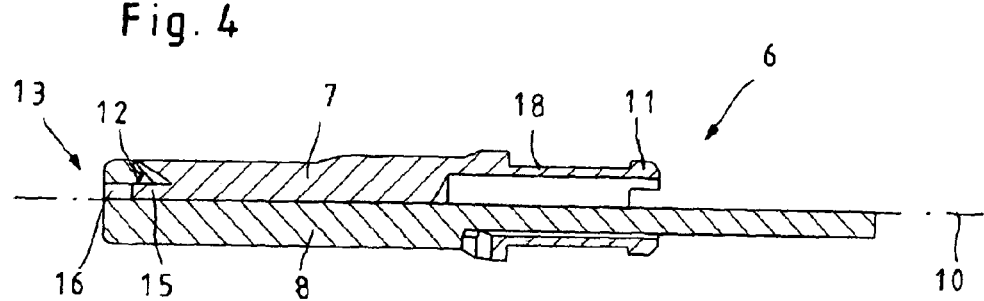
FIG. 4 is an enlarged cut-out view of detail III, showing a second inventive embodiment of a tool point.
Figure 5:
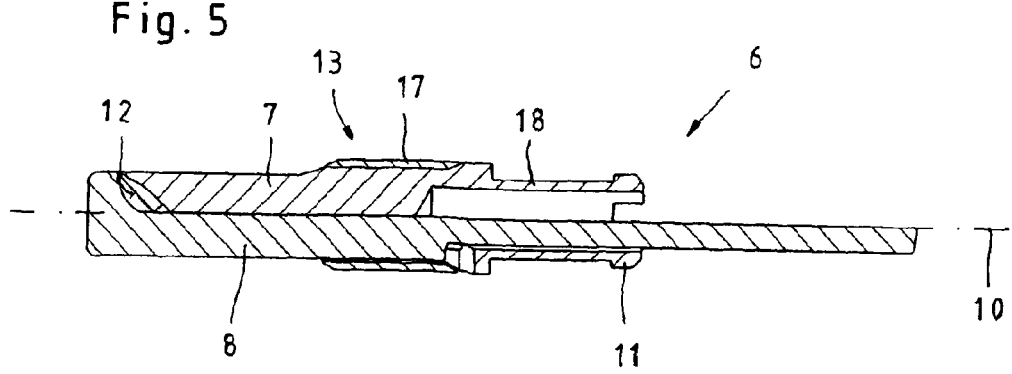
FIG. 5 is an enlarged cut-out view of detail III, showing a third inventive embodiment of a tool point.

To stabilize the cutting parts 7 and 8 in their axially parallel position to one another and to prevent their slipping apart, on each of the tool points 6 illustrated in FIGS. 3 through 5, one anti-tilt mechanism 13 is positioned that makes it impossible for the cutting parts 7 and 8 to be tilted.

In the first embodiment shown in FIG. 3, the anti-tilt mechanism 13 is configured as a thrust bearing 14 in the form of a bulge configured in the proximal area on the displaceable cutting part 1, with which the rigid cutting part 7 is contiguous and thus the axially parallel alignment of the cutting parts 7 and 8 to one another is fixed in place.

In the second embodiment for configuring the anti-tilt mechanism 13, shown in FIG. 4, the anti-tilt mechanism 13 is configured as a guide pin 15 that is positioned in the distal area on the rigid cutting part 7 and engages in a corresponding recess 16 in the displaceable cutting part 8 and thus fixes in place the axial parallel alignment of the cutting parts 7 and 8 to one another in the closed punch position.

In the third embodiment shown in FIG. 5, the anti-tilt mechanism 13 is configured as the sleeve 17 that surrounds both cutting parts 7 and 8 in the proximal area and as an external pressure sleeve fixes the two cutting parts 7 and 8 with respect to one another.

Common to all three illustrated embodiments is the fact that owing to the positioning of the anti-tilt mechanism 13 on the tool point 6, the slipping of the cutting parts 7 and 8 out of their axially parallel alignment to one another, as shown in FIG. 2 and known from the art, is prevented, so that the operator is always guaranteed an exact and calibrated actuation of the cutting parts 7 and 8 of the medical punch 1.

As can further be seen from FIGS. 3 through 6, the rigid cutting part 7 in all embodiments consists of a sleeve-shaped proximal portion 18 that encloses the displaceable cutting part 8 and a distal punch portion 19 that is configured as a single unit with the sleeve-shaped portion 18, such that a guide track 20 is configured in the sleeve-shaped proximal portion 18 of the rigid cutting part 7 to guide and receive the displaceable cutting part 8.

For inserting and guiding the displaceable cutting part 8, the guide track 20 is advantageously configured in such a way that it surrounds in essentially form-locking manner the external contour of the displaceable cutting part 8 that is to be inserted. The properly aligned guidance of the displaceable cutting part 8 in the guide track 20 is stabilized in the embodiments shown in FIGS. 6 and 7 thanks to the fact that guide elements 21 are configured on the displaceable cutting part 8 that protrude laterally outward and engage in a corresponding recess 22 of the guide track 20.

Figure 6:
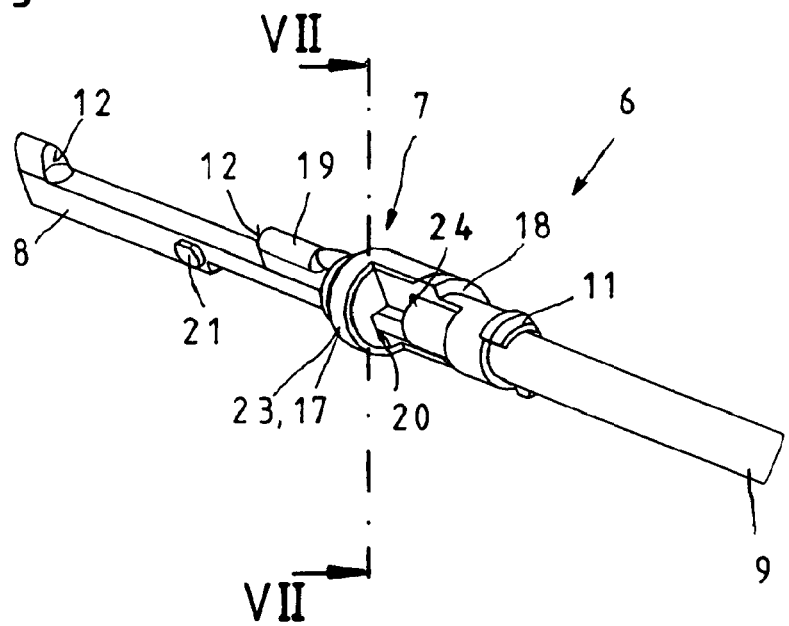
FIG. 6 is a partly cut-out perspective view of a fourth inventive embodiment of a tool point in the opened position.

The embodiment of the tool point 6 shown in FIG. 6 is differentiated from the embodiments shown in FIGS. 3 through 5 by the configuration of the cutting surfaces 12. While the cutting surfaces 12 of the cutting parts 7 and 8 in the embodiment in FIG. 6 are configured parallel to one another and essentially at a right angle to the longitudinal axis 10 of the shaft 2, the cutting surfaces 12 of the cutting parts 7 and 8 of the embodiments in FIGS. 3 through 6 are likewise parallel to one another but are configured at an angle that departs from the right angle, preferably at a 45 degree angle to the longitudinal axis 10 of the shaft 2.

The operational and functional modes of the illustrated and described medical punches 1, however, are completely independent of the alignment of the cutting surfaces 12 to the longitudinal axis 10 of the shaft 2.

Figure 7:
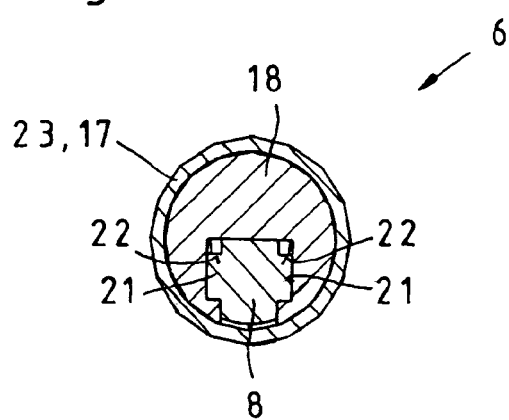
FIG. 7 is a sectional view along the line VII-VII of FIG. 6, but showing the tool point in the closed position.

To facilitate installation and dismantling of the tool point 6 with the two cutting parts 7 and 8, as can be seen in particular from FIGS. 6 and 7, the rigid cutting part 7 and the displaceable cutting part 8 are connected with one another by a sleeve-shaped enclosure 23 that is slid over the sleeve-shaped portion 18 of the rigid cutting part 7 to form a single component.

Thanks to this sleeve-shaped enclosure 23, the rigid cutting part 7 is undetachably affixed to the cutting part 8 that is displaceably mounted in the guide track 20 of the rigid cutting part 7, so that a single assembly unit is created that can be affixed to the hollow shaft 2 by means of the coupling mechanism 11 positioned on the sleeve-shaped proximal portion 18 of the rigid cutting part 7.

In the embodiment illustrated in FIGS. 6 and 7, the enclosure 23, which connects the displaceable cutting part 8 and the rigid cutting part 7 into a single component, also simultaneously forms the anti-tilt mechanism 13 that stabilizes the two cutting parts 7 and 8 with respect to one another and is configured as a sleeve 17.

As can also be seen from FIG. 6, a stop 24 is configured on the rigid cutting part 7 to restrict the displaceability of the displaceable cutting part 8 in the distal direction (open position).

A medical punch 1 of the configuration here described is characterized in that on the one hand it is of simple construction and allows an exact and well-calibrated actuation of the cutting parts 7 and 8, and on the other hand can be quickly and easily dismantled and reassembled for purposes of installation and cleaning.

The invention claimed is:

1. A medical punch with a hollow shaft, a tool point that is positioned on the distal end of the hollow shaft and comprises a rigid cutting part and a displaceable cutting part that can slide with respect to the rigid cutting part, and with a handle positioned on the proximal end of the hollow shaft, such that the displaceable cutting part and the handle are operatively connected with one another by a push/pull device that is displaceably mounted in the hollow shaft and an anti-tilt mechanism is positioned on the tool point to stabilize the cutting parts in their axially parallel alignment to one another, characterized in that the rigid cutting part comprises a sleeve-shaped proximal portion that encloses the displaceable cutting part and a distal punch portion that is configured as a single unit with the sleeve-shaped proximal portion, and in that the tool point comprises a sleeve-shaped enclosure that is slidable directly onto the sleeve-shaped proximal portion of the rigid cutting part for connecting the rigid cutting part and the displaceable cutting part to form a single assembly unit and wherein the single assembly unit is detachably connected with the hollow shaft by a coupling mechanism configured on the sleeve-shaped proximal portion, wherein the coupling mechanism is configured as a bayonet connection and wherein the anti-tilt mechanism is configured as the sleeve-shaped enclosure.

2. The medical punch according to claim 1, wherein a guide track for inserting the displaceable cutting part is configured in the sleeve-shaped proximal portion of the rigid cutting part.

3. The medical punch according to claim 2, wherein a guide element is configured on the displaceable cutting part to stabilize at least the displaceable cutting part in the guide track.

4. The medical punch according to claim 1, wherein the displaceable cutting part is connected in an at least force-fitted manner with the push/pull device.

5. The medical punch according to claim 1, wherein the push/pull device can be inserted into the hollow shaft and withdrawn from the hollow shaft by the distal end of the hollow shaft.

6. The medical punch according to claim 1, wherein a stop is configured on the rigid cutting part to restrict the displaceability of the displaceable cutting part in the distal direction.

* * * * *